(12) United States Patent
Rhyan

(10) Patent No.: US 11,806,476 B2
(45) Date of Patent: *Nov. 7, 2023

(54) SYSTEM AND METHOD FOR PORTABLE RETRACTABLE REELING

(71) Applicant: D'Andre Rhyan, Waukegan, IL (US)

(72) Inventor: D'Andre Rhyan, Waukegan, IL (US)

( * ) Notice: Subject to any disclaimer, the term of this patent is extended or adjusted under 35 U.S.C. 154(b) by 330 days.

This patent is subject to a terminal disclaimer.

(21) Appl. No.: 17/124,395

(22) Filed: Dec. 16, 2020

(65) Prior Publication Data

US 2021/0100971 A1 Apr. 8, 2021

Related U.S. Application Data

(63) Continuation-in-part of application No. 15/946,705, filed on Apr. 5, 2018, now Pat. No. 10,888,682.

(Continued)

(51) Int. Cl.
*A61M 16/06* (2006.01)
*B65H 75/44* (2006.01)
*B65H 75/40* (2006.01)

(52) U.S. Cl.
CPC ......... *A61M 16/0672* (2014.02); *B65H 75/40* (2013.01); *B65H 75/446* (2013.01); *B65H 75/4471* (2013.01); *B65H 75/4478* (2013.01); *B65H 75/4492* (2013.01); *A61M 2202/0208* (2013.01); *A61M 2209/06* (2013.01); *A61M 2209/088* (2013.01); *B65H 2701/33* (2013.01)

(58) Field of Classification Search
CPC .......... A61M 16/0666; A61M 16/0672; A61M 16/08; A61M 16/0875; A61M 2202/0208; A61M 2209/06; A61M 2209/08; A61M 2209/084; A61M 2209/086; A61M 2209/088; B65H 75/40; B65H 75/406; B65H 75/441; B65H 75/446; B65H 75/4468; B65H 75/4471; B65H 75/4478; B65H 75/4492; B65H 2701/33; B65H 57/12

See application file for complete search history.

(56) References Cited

U.S. PATENT DOCUMENTS 5,826,608 A 10/1998 Pierce
6,065,490 A 5/2000 Falcone, Jr.
(Continued)

FOREIGN PATENT DOCUMENTS

DE 202013100598 U1 * 4/2013 ............ B65H 75/40
DE 202013100598 U1 * 6/2013 ............ B65H 75/40

OTHER PUBLICATIONS

Machine translation of DE-202013100598-U1.*

*Primary Examiner* — Joseph D. Boecker
(74) *Attorney, Agent, or Firm* — Bold IP, PLLC; Christopher Mayle

(57) ABSTRACT

A portable retractable oxygen tubing reel providing improved portability and mechanical reeling functionality. The portable retractable oxygen tubing reel includes tubing wrapped around an inner circular component stored within an outer storage compartment whereby a handle attached to the inner circular component may be rotated to wind or unwind tubing from the portable retractable oxygen tubing reel. Tubing may then be connected to a medical oxygen storage device at one end and a nasal oxygen cannula positioned near in proximity to a patient's nose for breathing oxygen at the other end.

2 Claims, 6 Drawing Sheets

Related U.S. Application Data

(60) Provisional application No. 62/481,682, filed on Apr. 5, 2017.

(56) References Cited

U.S. PATENT DOCUMENTS

| | | |
|---|---|---|
| 6,591,858 B2 | 7/2003 | Peterson |
| 6,889,688 B1 | 5/2005 | Wright |
| 8,191,551 B2 * | 6/2012 | Skovgard |
| 10,221,037 B1 * | 3/2019 | Blasbalg ............ B65H 75/4402 |
| 10,888,682 B2 * | 1/2021 | Rhyan ................ B65H 75/4471 |
| 2002/0195143 A1 * | 12/2002 | Paplow .............. B65H 75/4471 |
| | | 137/355.2 |
| 2010/0307496 A1 * | 12/2010 | Lueckenhoff ...... B65H 75/4471 |
| | | 242/388 |
| 2016/0304311 A1 * | 10/2016 | Buck .................. B65H 75/4471 |
| 2018/0289915 A1 * | 10/2018 | Rhyan ................ B65H 75/446 |

* cited by examiner

SYSTEM AND METHOD FOR PORTABLE RETRACTABLE REELING

CROSS-REFERENCE TO RELATED APPLICATIONS

This application is a continuation in part of U.S. Non-Provisional application Ser. No. 15/946,705 filed on Apr. 5, 2018, which claims priority to U.S. Provisional Application No. 62/481,682, filed on Apr. 5, 2017. The content of the above application is hereby expressly incorporated by reference herein in its entirety.

FIELD OF DISCLOSURE

The overall field of this invention is a system and method for a tubing reel. More particularly, the invention is directed to a convenient oxygen tubing reel capable of attachment to a medical oxygen storage device to provide for increased mobility to a patient as well as to have the patient no longer encumbered by excessive slack when walking around the surrounding area.

BACKGROUND

One of the most often administered hospital treatments is oxygen therapy. Oxygen therapy is a treatment that delivers oxygen gas to assist a patient in breathing. Oxygen therapy may be provided from tubes resting in one's nose, via a face mask, or via a tube placed in one's trachea, or windpipe. This treatment may increase the amount of oxygen received in one's lungs and delivered through one's blood. Oxygen therapy may be prescribed for a wide variety of reasons including chronic obstructive pulmonary disease (COPD), which is a progressive chronic inflammatory lung disease that causes obstructed airflow from the lungs. Other reasons may include chronic bronchitis, emphysema, major trauma, anaphylaxis, major hemorrhage, shock, convulsions, and hypothermia. To provide the patient with more oxygen, large medical oxygen storage devices that are usually in the form of tanks holding compressed oxygen may be taken home when the patient leaves the hospital to continue treatment.

These tanks are usually large and awkward to carry around and can drastically decrease the patient's quality of life by limiting their mobility since continued treatment requires proximity to the medical oxygen storage device. Smaller more portable tanks have also been used, but these smaller tanks need to be refilled every few hours, which can be a bother. As well, many older patients in their increased age find the tanks difficult to move even with lesser weight.

Long lengths of tubing connected to the oxygen tank have also been used to extend one's range of movement, thus letting the patient be at a greater distance from the oxygen tank. However, tears, bends, and kinks appear quite frequently in the tubing, which is a problem. Additionally, the tubing can easily become wrapped around furniture or other objects located throughout a patients home or other surrounding area that the patient is located, thereby restricting the airflow within the tubing and preventing optimal oxygen delivery to the patient. Patients also have been reported to trip and fall over such large, added lengths of tubing.

Multiple methods and systems are currently available that allow the tubing to be spooled and unspooled so that only a minimal amount of tubing necessary is unreeled and exposed through the patient's home or other surrounding area. U.S. Pat. No. 6,591,858 uses a complicated array of ratcheting mechanisms, springs, and gears to coil and uncoil the tubing and proving to be far too mechanically complicated and bulkier. U.S. Pat. Nos. 6,889,688 and 5,826,608 are likewise large in size and have a complicated spring loaded spooling reel mechanism. The large size and complicated machinery of these devices decrease portability while increasing the device's price and repair costs. Other devices currently on the market use electricity to power their spooling mechanisms. The required proximity to an electrical source further decreases the portability of these units. Electric parts also lead to a higher price base and repair costs with more components that may become easily damaged.

Thus, a need for a system and method of using a truly portable tubing spooling providing storage with a manual retraction mechanism that can be produced and repaired cheaply exists.

SUMMARY

The present invention will be described by way of exemplary embodiments, but not limitations, illustrated in the accompanying drawings in which like references denote similar elements, and in which:

According to one embodiment, a portable retractable oxygen tubing reel that includes an inner component and an outer storage compartment, the inner component insertable within the outer storage component. Further, the inner component may be rotatable within the outer storage component. The outer storage compartment may have an opening. The inner component may include an upper and lower disc that may be connected by a cylinder, with the cylinder positioned in between the upper and lower discs whereby the outer storage compartment is an open cylinder covering only the cylinder of the inner component when the inner component is inserted into the outer storage compartment. In one embodiment, the cylinder, upper, and lower disc may have a hole pass through, as well as tubing that is configured to be wound around the cylinder of the inner component and fed through the hole and the opening. The portable retractable oxygen tubing reel may include a first handle, whereby the handle may be attached to the upper disc and may protrude in an outward direction. Further, an embodiment of the portable retractable oxygen tubing reel may include a second handle, the second handle being attached to an outer surface of the outer storage component.

According to one embodiment, a method of dispensing and retracting oxygen tubing may include connecting a first end of a length of tubing to a nasal oxygen cannula, winding tubing around a portable retractable oxygen tubing reel, the portable retractable oxygen tubing reel having an inner component and an outer storage compartment, the outer storage compartment having an opening and the inner component including an upper and lower disc connected by a cylinder. The cylinder may be positioned in between the upper and lower discs, whereby the cylinder, upper and lower disc may have a hole pass through. The portable retractable oxygen tubing reel, in one embodiment, may further include a handle, the handle being attached to the upper disc, which may protrude outwardly, with the tubing wound around the cylinder of the inner component. The inner compartment may be inserted into the outer storage component, and the tubing fed through the opening in the outer storage compartment. The method may further include connecting a second end of the tubing to a medical oxygen storage device, connecting the nasal oxygen cannula to a user's nose, including at least one of steps of the user moving forward, pulling on the tubing, rotating the handle in one direction causing the tubing to unspool from the cylinder, rotating the handle in a direction opposite of the first direction causing the tubing to spool around the cylinder, disconnecting the nasal oxygen cannula from the user's nose, and disconnecting the second end of the tubing from the medical oxygen storage device.

BRIEF DESCRIPTION OF DRAWINGS

The present invention will be described by way of exemplary embodiments, but not limitations, illustrated in the accompanying drawings in which like references denote similar elements, and in which.

DEFINITIONS

Figure 1:
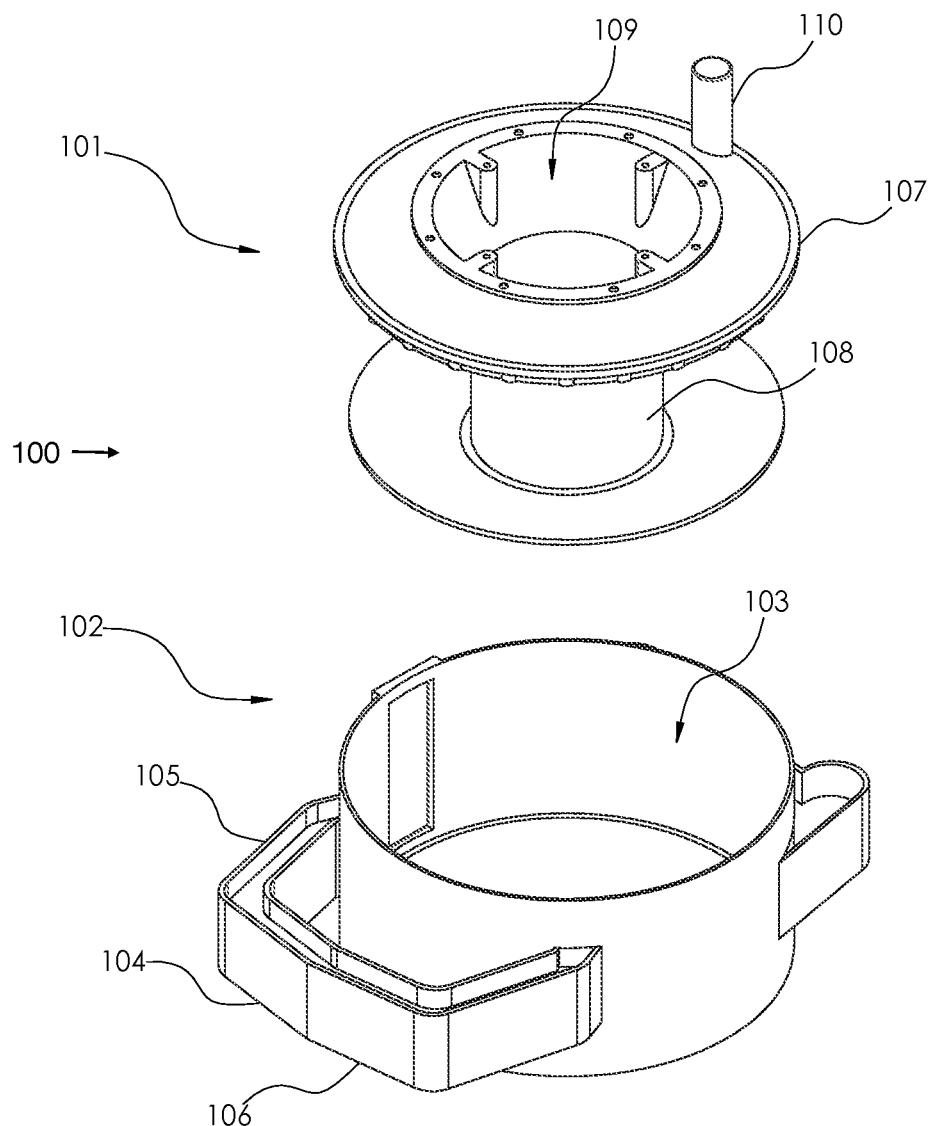
FIG. 1 is a exploded perspective, top-view illustration, showing a portable retractable reeling spool for medical line management in accordance with an illustrative embodiment.

Longitudinal axis: An imaginary generally straight line that runs through the center of the portable retractable reeling spool intersecting the square handle and the generally straight portion that connects the generally curved portions.

Latitudinal axis: An imaginary generally straight line that runs through the center of the portable retractable reeling spool perpendicular to the longitudinal axis and intersects both of the openings.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

"Exemplary" is used herein to mean "serving as an example, instance, or illustration." Any aspect described in this document as "exemplary" is not necessarily to be construed as preferred or advantageous over other aspects.

Throughout the drawings, like reference characters are used to designate like elements. As used herein, the term "coupled" or "coupling" may indicate a connection. The connection may be a direct or an indirect connection between one or more items. Further, the term "set" as used herein may denote one or more of any item, so a "set of items," may indicate the presence of only one item, or may indicate more items. Thus, the term "set" may be equivalent to "one or more" as used herein.

In the following detailed description, numerous specific details are set forth in order to provide a more thorough understanding of the one or more embodiments described herein. However, it will be apparent to one of ordinary skill in the art that the invention may be practiced without these specific details. In other instances, well-known features have not been described in detail to avoid unnecessarily complicating the description.

The present disclosure recognizes the unsolved need for a portable retractable reeling spool providing storage with a manual retraction mechanism. Unlike conventional devices, the portable retractable reeling spool does not need electricity, lacks mechanical complication, and is small enough in size that anyone can easily carry it around the house. Oxygen tubing enters from a medical oxygen storage device through one side of the portable retractable reeling spool. The tubing then wraps around the central hub of the portable retractable reeling spool such that it lies flush with the central hub and exits through another hole where the tubing may be attached to a nasal oxygen cannula or other apparatus. To use the portable retractable reeling spool, the patient may easily pull on the oxygen tubing which is able to reel out of the portable retractable reeling spool. To return the tubing back into the portable retractable reeling spool 100, the patient can manually wind up the device using an attached handle.

FIG. 1 depicts a non-limiting embodiment of portable retractable reeling spool 100. Portable retractable reeling spool 100 may include an inner circular component such as inner component 101 and an outer storage component such as outer storage component 102. Outer storage component 102 may have a hollow central circular portion such as hollow central circular portion 103. Central circular portion 103 may be connected to a handle such as handle 104. Handle 104 is depicted to be square in shape, however this is non-limiting and handle 104 may be a rectangle, circle, semicircle, hexagon, octagon, prism, horseshoe, rod, trapezoid, or any other suitable shape. For example, in some embodiments an arcuate handle may be used.

Handle 104 may have two generally straight portions such as portions 105 extending from central circular portion 103 parallel to portable retractable reeling spool's 100 longitudinal axis. Portions 105 may be parallel to portable retractable reeling spool's 100 longitudinal axis and may be connected by a generally straight portion such as portion 106 that runs parallel to portable retractable reeling spool's 100 latitudinal axis. In some embodiments, straps 410, illustrated in FIG. 6, may also be used to tie portable retractable reeling spool around the patient's waist or to hang portable retractable reeling spool 100 from the patient's shoulder to further secure portable retractable reeling spool 100 to the patient and reduce the needed effort in carrying portable retractable reeling spool 100 around the surrounding area.

Figure 2:
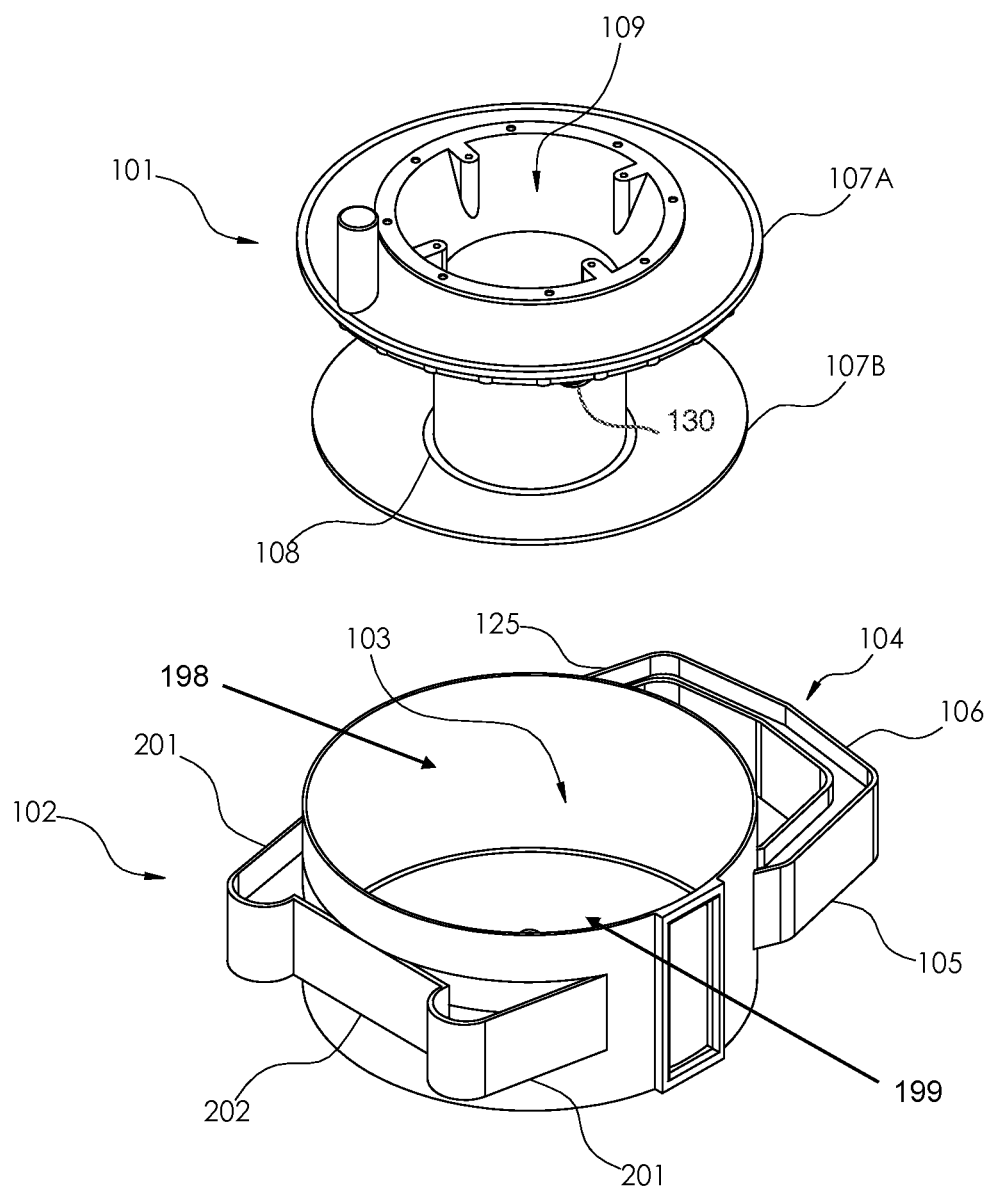
FIG. 2 shows an exploded perspective view of the portable retractable reeling spool in accordance with an illustrative embodiment.

At the bottom of central circular portion 103 may be at least two generally curved portions such as portions 201, as best seen in FIG. 2, that allow portable retractable reeling spool 100 to stand upright on a horizontal surface such as a table for storage and stability. At least one of portions 201 may extend generally parallel to portable retractable reeling spool's 100 latitudinal axis, from each side of the bottom of portable retractable reeling spool 100. Portions 201 are connected by a generally straight portion such as portion 202 that runs generally parallel to portable retractable reeling spool's 100 latitudinal axis. Other methods to keep portable retractable reeling spool 100 upright on a horizontal surface may be used such as fastening plurality of studs or knobs on the bottom of central circular portion 103. Studs may be of any shape and size including being in the shape of a cube, pyramid, prism, cylinder, or sphere. The bottom side of portion 202 may include an additional gripping surface material or any suitable adhesive, so that either the surface material or adhesive may prevent slippage between portable retractable reeling spool 100 and another surface.

Inner component 101 may have two circular disc sections such as circular disc sections 107A and 107B connected by a circular tubular section such as circular tubular section 108. Circular disc sections 107A, 107B may extend radially past central circular tubular section 108 on the upper and lower ends of central circular tubular section 108. Central circular tubular section 108 may extend vertically upwards between circular disc sections 107A and 107B, which are respectively oriented horizontally.

FIG. 3a, 3b, 3c, 3d shows the inner component 101 inserted into outer storage component 102 or in an assembled view. As shown in FIG. 3a, 3b, 3c, 3d, circular disc section 107A and circular disc 107b are visible after inner component 101 is inserted into outer storage component 102 whereby outer storage component 102 is an open cylinder covering only the cylinder of inner component 101 when inner component 101 is inserted into outer storage compartment 102. When inserted inner component 101 may pass through opening 198 or opening 199 of outer storage component 102. In one embodiment, circular disc section 107A may have an opening such as opening 109. In one embodiment, opening 109 may be 5 inches in diameter, although those of ordinary skill in the art will appreciate that any suitable diameter may be used. A tubular handle, such as tubular handle 110, may rotate inner component 101. Tubular handle 110 may be attached to the periphery of circular disc 107A and may extend outwardly and parallel to the axis of rotation. Tubular handle 110 extends from the non-hollow portion of circular disc section 107A perpendicularly to portable retractable reeling spool's 100 longitudinal and latitudinal axes.

In one embodiment, the length between circular disc sections 107A and 107B, and thus the length of central tubular section 108, may be five inches. Additional exemplary dimensions for the inner component 101 may be 3×5¼×5⅜ inches. Outer storage component 102 may preferably be 2×⅜×5½ inches. Further, it may be preferable for there to be enough space between inner component 101 and the outer storage component 102 to facilitate the ease of reeling. It is noted that the above-listed dimensions are non-limiting and any size or dimension may be used based on the specific needs of the oxygen delivery requirements as well as the size of the oxygen tubing and medical oxygen storage device.

Figure 3A:
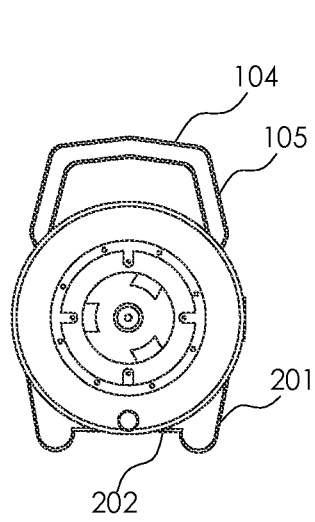
FIG. 3a is front-view illustration, showing the assembled portable retractable reeling spool in accordance with an illustrative embodiment.
Figure 3B:
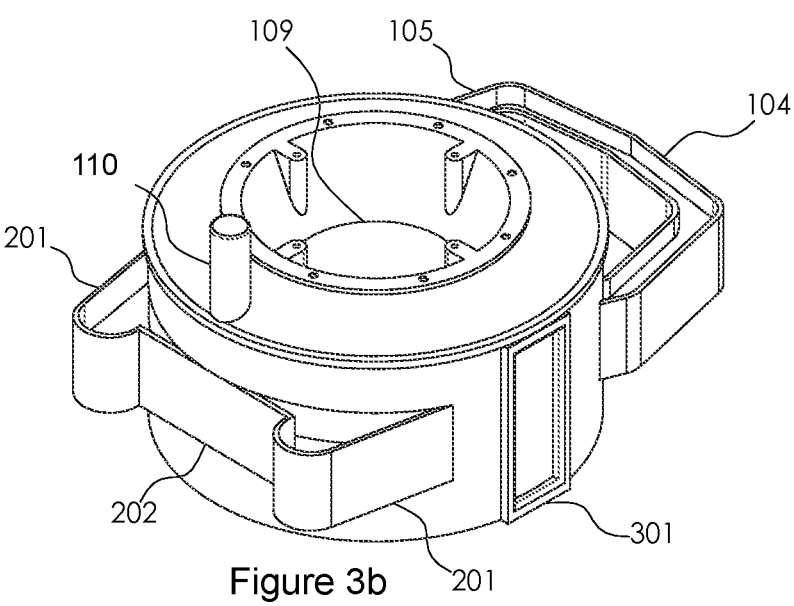
FIG. 3b is a perspective illustration, showing the assembled portable retractable reeling spool in accordance with an illustrative embodiment.
Figure 3C:
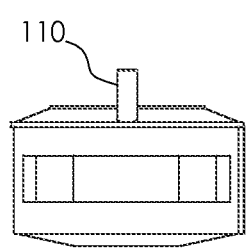
FIG. 3c is top-view illustration, showing the assembled portable retractable reeling spool in accordance with an illustrative embodiment.
Figure 3D:
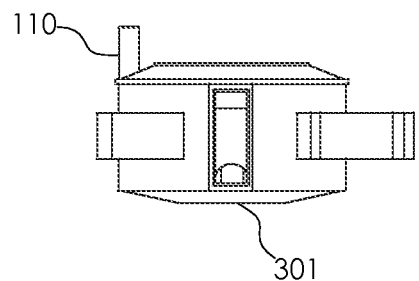
FIG. 3d is side-view illustration, showing the assembled portable retractable reeling spool in accordance with an illustrative embodiment.

Inner component 101 may be connected to outer storage component 102 using a swivel or other suitable connector, allowing inner component 101 to spin freely. One opening such as opening 301 (e.g. as shown in FIG. 3d) may exist on each of the side walls of central circular portion 103 along with opening 109 on the top face of circular disc section 107A of the inner component 101.

Figure 4:
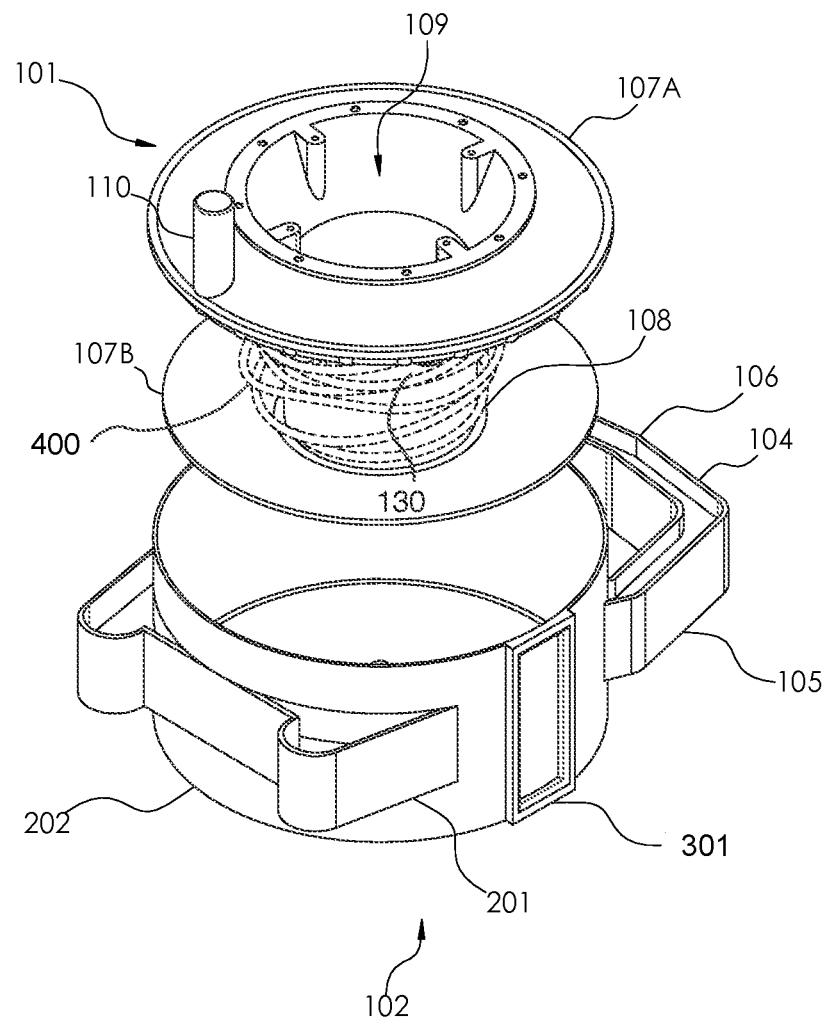
FIG. 4 is a perspective, top-view illustration, showing the tubing wrapped around the central hub of the portable retractable reeling spool in accordance with an illustrative embodiment.
Figure 5:
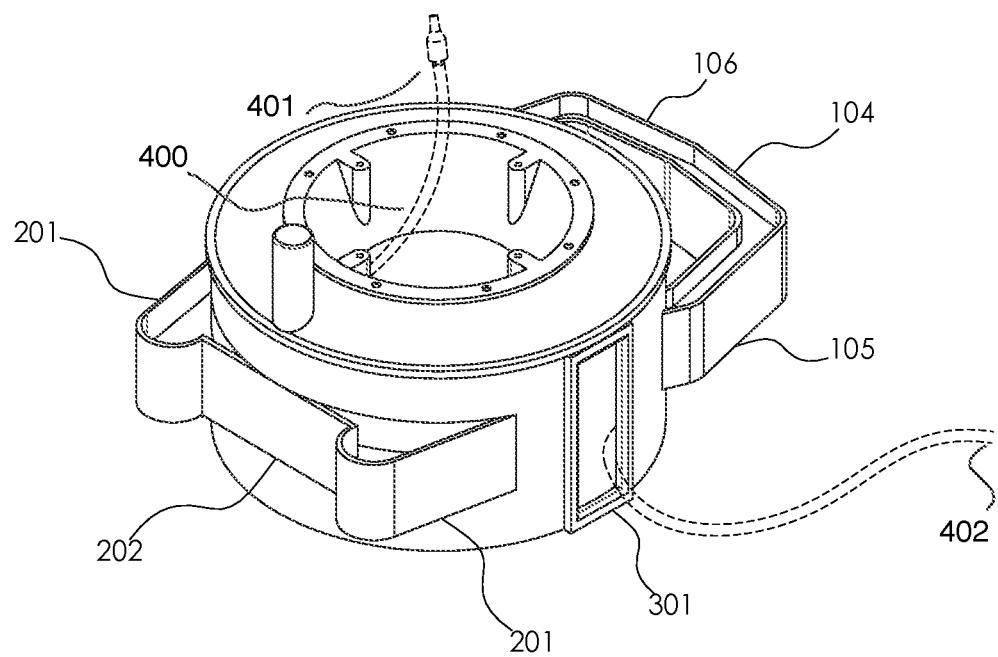
FIG. 5 is a perspective, top-view illustration, of an inner component assembled together with the outer storage component of the portable retractable reeling spool, and further shows the tubing of the portable retractable reeling spool exiting through a center opening and exiting out the portable retractable reeling spool through another hole in accordance with an illustrative embodiment.

In one embodiment, tubing, such as tubing 400, shown in FIG. 4, may enter through opening 301 and wrap around central tubular section 108 (e.g. as shown in FIG. 2 and FIG. 4) before exiting through opening 109 (e.g. as shown in FIG. 5) in the top face of circular disc section 107A. In one embodiment, only 2 to 3 inches of tubing 400 protrudes out of opening 109. At least one guide, such as guide 130 (e.g. as shown in FIGS. 2 and 4), may be present on central tubular section 108, keeping tubing 400 flush against central tubular section 108.

Tubular handle 110, extending away from the top face of circular disc section 107A, is configured to turn inner component 101 and to retract tubing 400 into portable retractable reeling spool 100. Both the front and back of portable retractable reeling spool 100 may be enclosed except for opening 301 and opening 109 where tubing 400 enters and leaves portable retractable reeling spool 100.

Portable retractable reeling spool 100 components may be made from any suitable material known in the art. In one embodiment, portable retractable reeling spool 100 may be made out of plastic, which may be sterilized through systems such as an autoclave, having elevated steam temperature and pressure different from ambient air pressure to kill bacteria, spores and germs resistant to boiling water and powerful detergents. Alternatively, handle 104, portions 201, and portion 202, may be made of any material suitable to provide structural stability needed for the portable retractable reeling spool 100. In one exemplary embodiment, it may be preferable for portable retractable reeling spool 100 to weigh less than two pounds. Further, it may be beneficial for portable retractable reeling spool 100 to be no larger than 30 inches across to be less of a hindrance while being carried by a patient. These dimensions and weight are however non-limiting and may be varied and altered in any way as needed to suit the user. Further considerations may include the specific needs of the oxygen delivery requirements as well as the size of the tubing and medical oxygen storage device.

Figure 6:
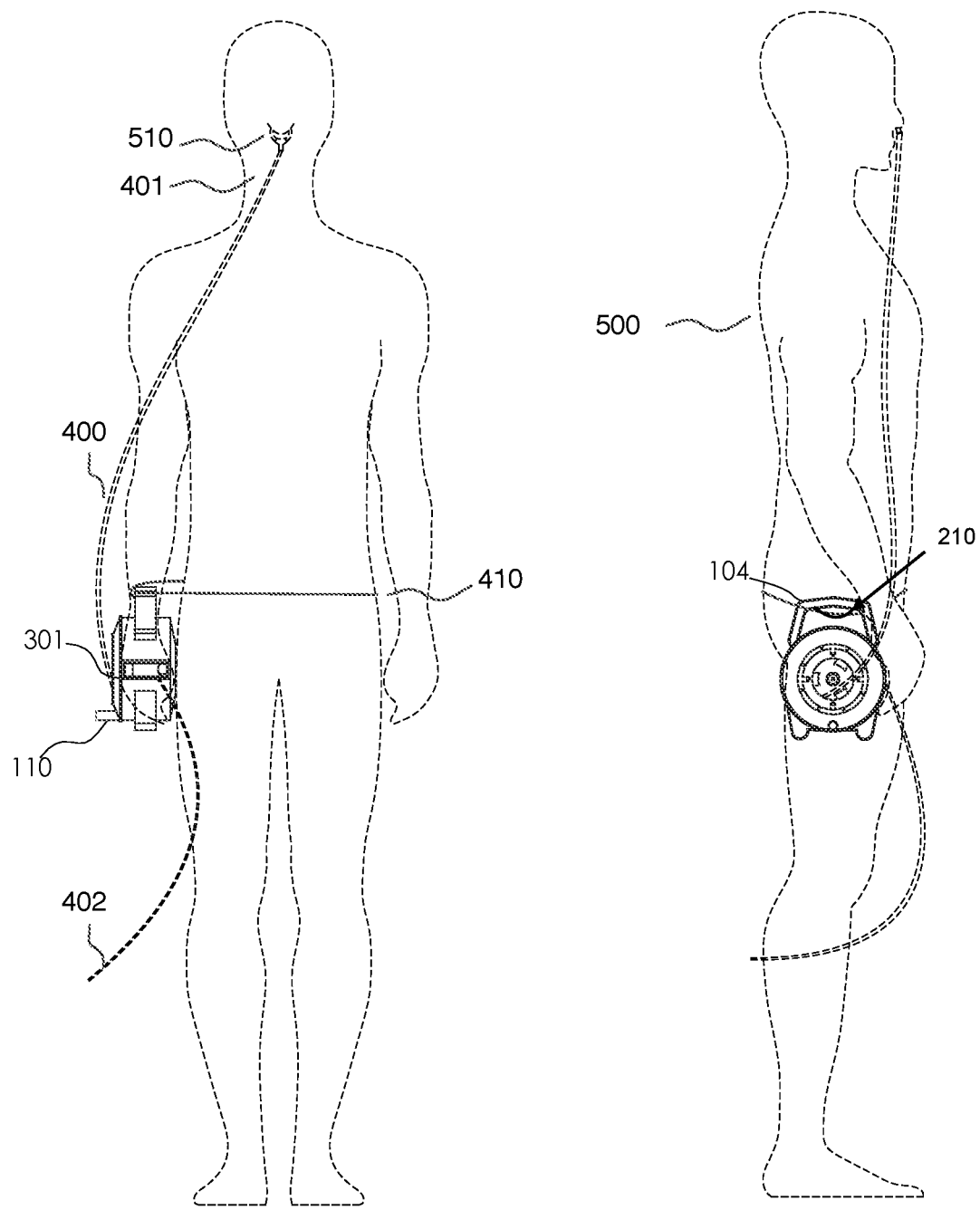
FIG. 6 is an illustration, showing the portable retractable reeling spool in use on a patient in accordance with an illustrative embodiment.

FIG. 6 may show portable retractable reeling spool 100 and one exemplary method of its use. As shown in FIG. 6, a first end such as first end 401 of the tubing 400 is pulled through opening 109 with first end 401 connected to a nasal oxygen cannula or other apparatus such as nasal oxygen cannula 510 suitable for being positioned near in proximity to a patient, such as patient 500, for purposes of assisting patient 500 in breathing oxygen. Nasal oxygen cannula 510 may be any suitable type of nasal oxygen cannula as known in the art. Nasal oxygen cannula 510, in one embodiment, may include plastic tubing that fits behind the ears of patient 500 and further includes a set of prongs that are placed in the nostril of patient 500. A nasal oxygen cannula, such as nasal oxygen cannula 510, helps to provide supplemental oxygen to patient 500.

Continuing with a method of using portable retractable reeling spool 100, in one embodiment, the rest of tubing 400 is then wrapped around central tubular section 108. Inner component 101 is then inserted into outer storage compartment 102. Once inner component 101 is inserted into outer storage compartment 102, the second end such as second end 402 of tubing 400 is threaded through opening 301 suitable for being connected to a medical oxygen storage device (not shown). Nasal oxygen cannula 510 is then positioned near in proximity to a patient's 500 nose for breathing oxygen. Patient 500 may fasten a strap such as strap 410 around handle 104 of portable retractable reeling spool 100 and patient's 500 waist to further secure portable retractable reeling spool 100 to patient 500. Strap 410 may be more securely connected to holding handle 104 by passing through a receiving element 210 that extends downward from the lower surface of holding handle 104. Receiving element 210 may have one or more gripping mechanism or flaps to prevent the movement once strap 410 is positioned through receiving element 210 unless sufficient force is used to remove strap 410.

When patient 500 wishes to extend tubing 400 to provide more slack, patient 500 may either move forward and tubing 400 will naturally unspool, pull on tubing 400 as it exits the portable retractable reeling spool 100, or rotate inner component 101 using tubular handle 110. To retract tubing 400 into portable retractable reeling spool 100, tubular handle 110 may be rotated in the opposite direction from the direction used to unspool tubing 400.

Portable retractable reeling spool 100 may be removed from patient 500 after use by detaching nasal oxygen cannula 510 from patient's 500 nose, removing tubing 400 from the medical oxygen storage device, and reeling in tubing 400 by rotating inner component 101 using handle 110 in the opposite direction from the direction used to unspool tubing 400. Portable retractable reeling spool 100 may then be placed on a horizontal surface or stored for subsequent use.

Tubing 400 may be replaced by detaching nasal oxygen cannula 510 and reeling in tubing 400 by rotating inner component 101 using tubular handle 110 in the opposite direction from the direction used to unspool tubing 400. Inner component 101 is then removed from outer storage compartment 102. Tubing 400 is then pulled out of opening 109 and unwound from central tubular section 108. Tubing 400 then may be replaced by new tubing. Cleaning of tubing 400 should not be attempted without proper guidance or the necessary equipment.

Embodiments for a portable retractable spooling reel have been provided herein, which may allow for a patient to receive oxygen from a medical oxygen storage device at a greater distance and with less difficulty than conventional devices. Further, the embodiments provided herein offer a mechanically advantageous way to dispense and retract the length of the tubing from one or more embodiments of a portable retractable spooling reel that allows for greater free movement to the patient as well as prevents excess tubing from being caught or restricted by objects in the surrounding area.

The foregoing description of the invention has been presented for purposes of illustration and description and is not intended to be exhaustive or to limit the invention to the precise form disclosed. Many modifications and variations are possible in light of the above teaching. The embodiments were chosen and described to best explain the principles of the invention and its practical application to thereby enable others skilled in the art to best use the invention in various embodiments and with various modifications suited to the use contemplated. The scope of the invention is to be defined by the above claims.

What is claimed is:

1. A portable retractable oxygen tubing reel comprising:
an inner component and an outer storage compartment, wherein the inner component is removably insertable within an aperture through the outer storage compartment, the inner component rotatable within the outer storage compartment, the outer storage compartment having an opening, the inner component comprising an upper disc and a lower disc, the upper disc and the lower disc connected by a cylinder, the cylinder positioned in between the upper disc and the lower disc, a hole passing through the upper disc and the lower disc and the cylinder, wherein the upper disc extends past the outer storage component on a side of the outer storage component;
tubing configured to be wound around the cylinder of the inner component and fed through the hole and the opening; and
a nasal oxygen cannula, the nasal oxygen cannula configured to be connected to a first end of the tubing.

2. A portable retractable oxygen tubing reel comprising: an inner component and an outer storage compartment, the inner component removably insertable within an aperture through the outer storage compartment, the inner component rotatable within the outer storage compartment, the outer storage compartment having an opening, the inner component comprising an upper disc and a lower disc, the upper disc and the lower disc connected by a cylinder, the cylinder positioned in between the upper disc and the lower disc, a hole passing through the upper disc and the lower disc and the cylinder; the upper disc accessible and viewable when the inner component is inserted into the outer storage compartment; tubing configured to be wound around the cylinder of the inner component and fed through the hole and the opening; a nasal oxygen cannula, the nasal oxygen cannula removably connected to a first end of the tubing.

\* \* \* \* \*